United States Patent [19]

Swicegood et al.

[11] Patent Number: 5,000,169
[45] Date of Patent: Mar. 19, 1991

[54] ADJUSTABLE FLEXION-EXTENSION HINGE FOR HINGED LIMB IMMOBILIZER

[75] Inventors: George D. Swicegood, Hiddenite; Henry L. Richbourg, Jr., Charlotte, both of N.C.

[73] Assignee: Clinitex Corporation, Huntersville, N.C.

[21] Appl. No.: 465,307

[22] Filed: Jan. 16, 1990

[51] Int. Cl.⁵ .................... A61F 3/00; A61F 5/00; A61F 5/37; A61F 5/04
[52] U.S. Cl. ...................... 128/80 C; 128/80 F; 128/882; 128/88
[58] Field of Search ............... 128/878, 882, 80 R, 128/80 C, 80 D, 80 F, 80 G, 879, 88, 87 R

[56] References Cited

U.S. PATENT DOCUMENTS

| | | | |
|---|---|---|---|
| 4,088,130 | 5/1978 | Applegate | 128/80 F |
| 4,463,751 | 8/1984 | Bledsoe | 128/80 C |
| 4,523,585 | 6/1985 | Lamb | 128/80 C |
| 4,554,913 | 11/1985 | Womack | 128/80 C |
| 4,599,998 | 7/1986 | Castillo | 128/80 C |
| 4,620,532 | 11/1986 | Houswerth | 128/80 C |
| 4,628,916 | 12/1986 | Lerman | 128/80 C |
| 4,697,583 | 10/1987 | Mason | 128/80 C |
| 4,732,143 | 3/1988 | Kausek | 128/80 C |
| 4,773,404 | 9/1988 | Townsend | 128/80 C |
| 4,856,500 | 8/1989 | Spademan | 128/80 C |

Primary Examiner—Robert A. Hafer
Assistant Examiner—Michael Brown
Attorney, Agent, or Firm—Ralph H. Dougherty

[57] ABSTRACT

A hinged limb immobilizer device for setting and securely maintaining a predefined range of motion for a limb, requires no special tools for installation or adjustment. Limit stops are adjusted by simply loosening the appropriate thumbscrew, and moving the limit stop to the prescribed setting. Separate color-coded, labelled scales for flexion and extension match-up with separate color-coded thumbscrews to avoid misunderstandings. Security of adjustment is optimized by limit stops which embody both friction stop and positive stop characteristics, resulting in a unique "three-point locking" mechanism.

13 Claims, 2 Drawing Sheets

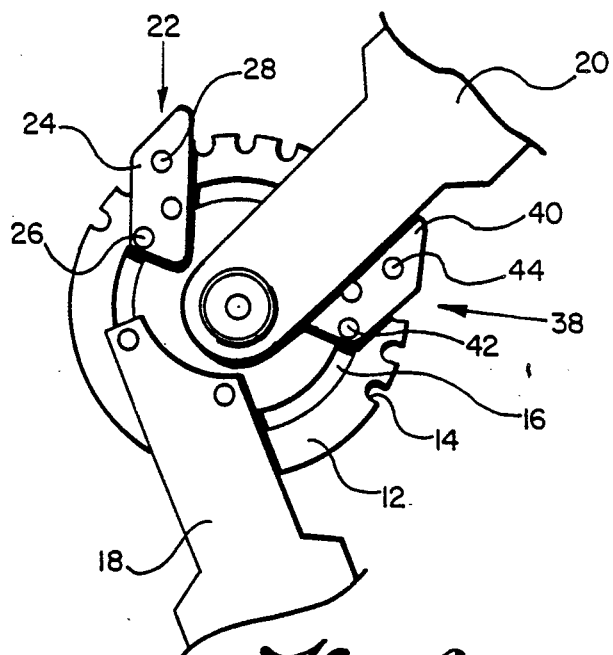
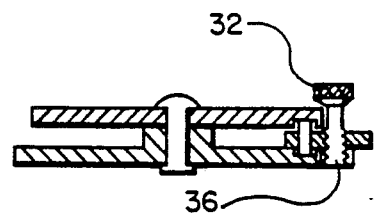
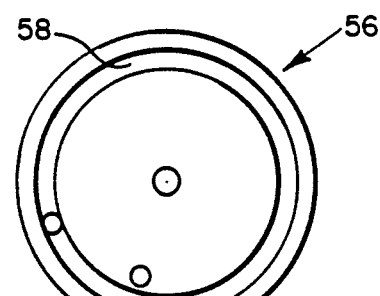
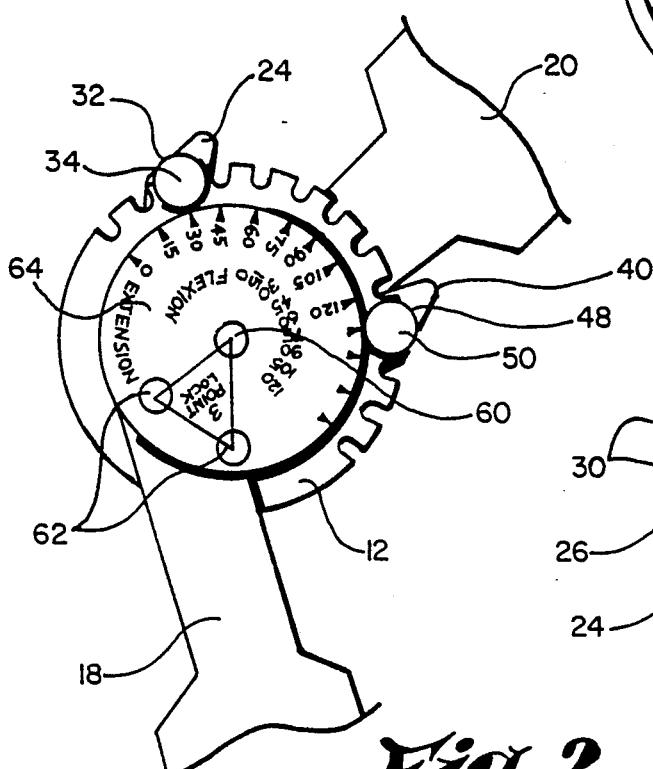
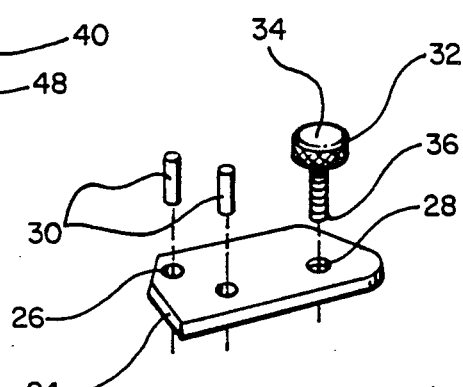

ADJUSTABLE FLEXION-EXTENSION HINGE FOR HINGED LIMB IMMOBILIZER

BACKGROUND OF THE INVENTION

1. Field of the Invention

The present invention generally relates to hinges and, more particularly, to a hinged limb immobilizer.

2. Description of the Prior Art

A frequently used method of post-operative ligament rehabilitation involves allowing restrictive but progressive motion of a limb, such as an arm, leg, or foot. Hinged limb immobilizers have been developed which allow the range of flexion-extension to be selectively set. "Flexion" refers to the act of bending a limb so as to decrease the angle formed by the limb, as in the act of flexing one's arm muscle. "Extension" means the opposite of flexion, as in the act of fully extending one's arm or leg. Two factors primarily determine the effectiveness of these immobilizers: (1) the security of the "limit stops" which define the allowable range of motion; and (2) the method of setting and adjusting these stops. Limit stops are typically either friction stops or positive stops. Friction stops provide the least security, since continued impact of the hinge against the stop can result in loosening, and gradual changes in the preset allowable range of motion. Positive stops are subject to bending and breakage through continued impact loading if the stops are small enough to allow desirable narrow incremental adjustments. If large enough for sufficient mechanical integrity, positive stops often fail to provide the desired level of adjustability. Current means for setting the limit stops may involve removable components which can be lost, or may require special tools which could be misplaced or otherwise unavailable when needed. Methods of adjustment may also be cumbersome or confusing for the wearer of the brace. Each of the preceding situations can result in compromised treatment, which can subsequently cause reinjury or impairment of the healing process.

The applicants are aware of the following U.S. patents concerning limb immobilizers.

with slide elements. It is the closest reference to the present invention, but requires the use of special tools to adjust the device. In addition, Houswerth does not include the three-point locking mechanism of the present invention. Mauldin, et.al., teaches a knee and elbow brace using a threaded bolt as a positive stop and also using a spring means in conjunction with the brace for assisting extension of the knee. Womack, et.al., relates to an adjustable joint for a knee brace with positive stops.

Lerman and Foster both teach knee braces using friction stops. Feanny, et.al., generally, relates to a brace for a knee and is not seen to be any more relevant than the previously discussed references.

Finally, Steinmann relates to an artificial knee-joint for supporting a natural knee. Although stops are provided, they appear to be positive stops and, moreover, do not appear to be adjustable.

Each of the prior art references cited above suffer from the disadvantages previously discussed. Applicants are unaware of any prior art that accomplishes the objects of the present invention. Consequently, a need exists for the invented hinged limb immobilizer.

SUMMARY OF THE INVENTION

The present invention is an innovative hinged limb immobilizer, which overcomes the problems and satisfies the needs previously considered.

The hinged limb immobilizer for a limb comprises a base, a first arm member affixed to a portion of the base and extending outwardly from and parallel to the base, a second arm member rotatably mounted to the base so that the second arm member rotates about the center of and parallel to the base, adjustable flexion and extension stopping means for stopping the second arm member, means for securing the first and second arm members and the adjustable extension and flexion stopping means to the base, and means for attaching the hinged limb immobilizer to the limb.

In summary, the invention provides a simple, logical device for setting and securely maintaining a predefined range of motion for a hinged limb immobilizer, requir-

|  | Issue Date | Inventor | Title |
| --- | --- | --- | --- |
| U.S. Pat. No. | | | |
| 4,620,532 | Nov. 4, 1986 | Houswerth | ADJUSTMENT DEVICE FOR AN ARTICULATED JOINT BRACE |
| 4,370,977 | Feb. 1, 1983 | Mauldin, et al. | KNEE AND ELBOW BRACE |
| 4,554,913 | Nov. 26, 1985 | Womack, et al. | ADJUSTABLE JOINT FOR A KNEE BRACE |
| 4,337,764 | Jul. 6, 1982 | Lerman | ADJUSTABLE MOTION BRACE |
| 4,506,661 | Mar. 26, 1985 | Foster | BALANCED SUSPENSION KNEE BRACE |
| 4,487,200 | Dec. 11, 1984 | Feanny, et al. | BRACE FOR KNEE |
| GER Pat. No. | | | |
| 412,362 | Apr. 17, 1925 | Steinmann | KUNSTLICHES KNIEGELENK ZUR UNTERSTUTZUNG DES NATURLICHEN KNIEGELENKES (ARTIFICIAL KNEE-JOINT FOR SUPPORTING A NATURAL KNEE JOINT) |

Houswerth, Mauldin, et.al., and Womack, et.al., all relate to joint braces using positive stop mechanisms. Houswerth discloses an adjustment device for an articulated joint brace having positive stops in conjunction ing no special tools. Limit stops are adjusted by simply loosening the appropriate thumbscrew, and moving the limit stop to the prescribed setting. Separate color-coded, labelled scales for flexion and extension match-up with separate color-coded thumbscrews to avoid misunderstandings. Security of adjustment is optimized by limit stops which embody both friction stop and positive stop characteristics, resulting in a unique "three-point locking" mechanism. Continued impact of a hinge against a conventional friction stop usually causes gradual progressive movement of the stop. In the current invention, pressure or impact against the stop imparts a "moment" which serves to lock it more securely into position. This effect additionally reduces the tendency of the positive mechanical stop (i.e., the thumbscrew) to loosen, but even in the event that it does become loose, the security of the stop is not compromised unless the thumbscrew is completely backed out. The current invention is also simple to manufacture. It was designed to be made from metal "stampings" instead of machined parts, thus resulting in consistent products at a controllable manufacturing cost.

OBJECTS OF THE INVENTION

The principal object of the present invention is to provide a hinged limb immobilizer for a human limb having a joint therein.

It is also an object of this invention to provide a hinged limb immobilizer having a predetermined range of motion.

It is also an object of this invention to provide a hinged limb immobilizer with a readily changeable range of motion.

It is also an object of this invention to provide a hinged limb immobilizer having a predefined range of motion which can be set and securely maintained without requiring special tools.

Another object of the invention is to provide an adjustable hinged limb immobilizer with security of adjustment in which limit stops embody both friction stop and positive stop characteristics, resulting in a unique "three-point locking" mechanism.

Another object of the invention is to provide a hinged limb immobilizer having separate color-coded, labelled scales for flexion and extension match-up with separate color-coded thumbscrews to avoid misunderstandings.

Yet another object of the invention is to provide a hinged limb immobilizer which is simple to manufacture, having parts made from metal "stampings" instead of machined parts, thus resulting in consistent products at a controllable manufacturing cost.

Still another object of this invention is to provide a method for setting and securely maintaining a predetermined range of motion of a hinged limb immobilizer, and for adjusting the range of motion, as desired.

Another object of the invention is to provide a comfortable means of attaching the hinged limb immobilizer to the limb.

BRIEF DESCRIPTION OF THE DRAWINGS

The foregoing and other objects will become more readily apparent by referring to the following detailed description and the appended drawings in which:

FIG. 2 is an enlarged plan view of the hinge portion of the invention shown in FIG. 1.

FIG. 3 is a plan view of the hinge portion of the invention shown in FIG. 2, with the cover or cap removed.

FIG. 4 is a plan view of the underside of the hinge cap or cover.

FIG. 5 is an exploded isometric view of a limit stop portion of the invention shown in FIG. 3.

FIG. 6 is a sectional view of a portion of the hinge base and cap taken through the hinge pivot and locking screw.

DETAILED DESCRIPTION

Figure 1:
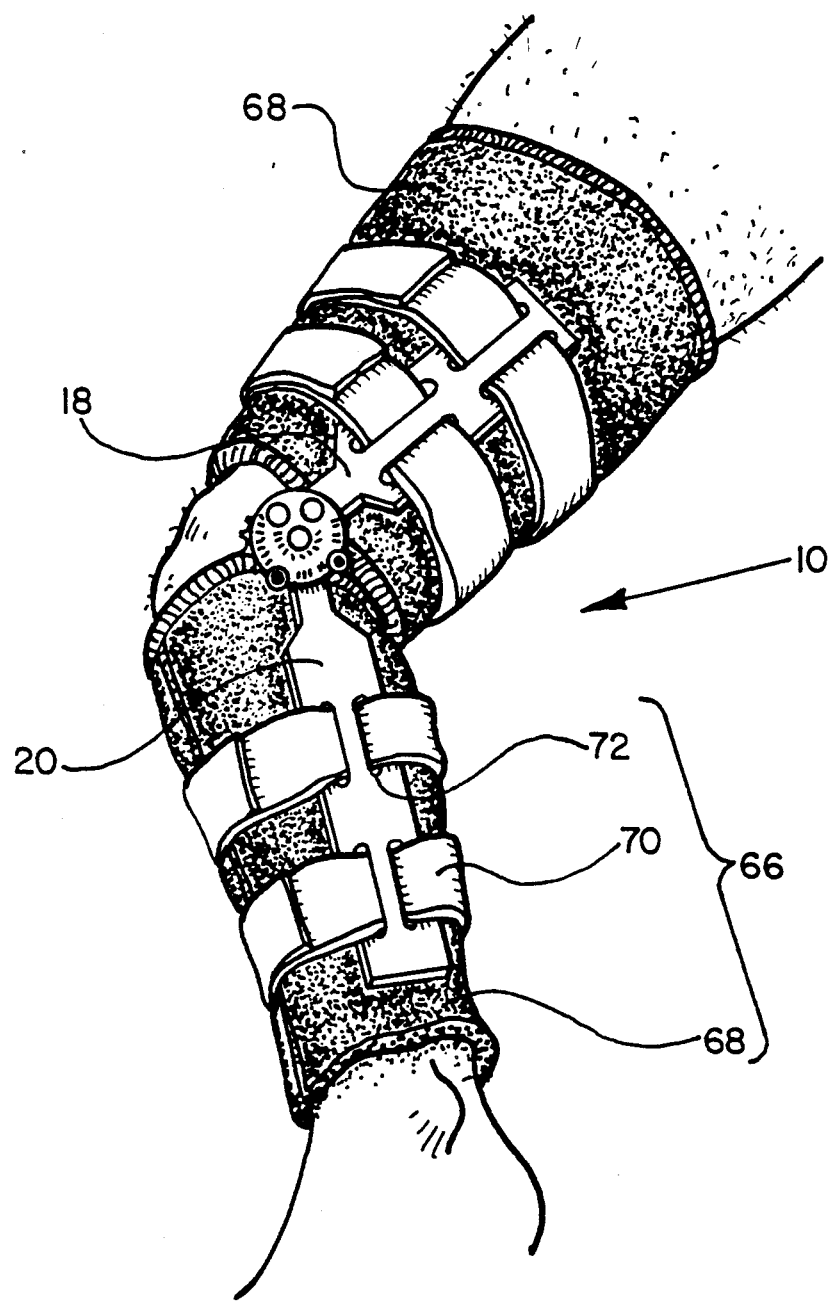
FIG. 1 is an isometric view of the invented hinged limb shown in use on a human knee.

Referring now to the drawings, and more particularly, to FIG. 1, a hinged limb immobilizer, generally designated 10, comprises the preferred embodiment of the present invention.

The hinged limb immobilizer 10 includes a generally round base plate 12 having circumferential indentations 14 for receiving manually insertable positive locking mechanisms 32, 48, e.g., thumbscrews, and an interior generally round recessed track 16 for receiving pins 30, shown in FIGS. 3 and 6. FIGS. 2 and 3 show that a first arm member 18 is affixed to the base 12 and extends outwardly from and parallel to the base 12. A second arm member 20 is pivotally connected to the base 12 so that the second arm member 20 is rotatable about the center of and parallel to the base 12, as shown in FIG. 3.

In the preferred embodiment, as shown in FIG. 3, an adjustable extension stopping means 22 for limiting the motion of the second arm member 20, and thereby limiting extension of the limb, is positioned between the first arm member 18 and the second arm member 20, and includes a first limit stop 24 having at least one pierced hole 26 and one tapped hole 28. Each pierced hole 26 is alignable with the interior rounded recessed track 16 of the base 12, and the tapped hole 28 simultaneously alignable with the associated indentation 14. Pins 30, equal to the number of pierced holes 26, are inserted into the pierced holes 26, and extend into the interior rounded recessed track 16 of the base 12. An extension thumbscrew 32, or other manually insertable positive locking mechanism, is inserted into the tapped hole 28 and engages the associated indentation 14 so that rotation of the second arm member 20 can be limited. In the preferred embodiment, two pierced holes 26, with associated pins 30, and the tapped hole 28, with associated extension thumbscrew 32, form a three-point extension locking mechanism. The extension thumbscrew 32, can be provided with a color coded extension decal 34 on its top face, and can have a swaged lower end 36 so as to prevent its removal from the first limit stop 24.

An adjustable flexion stopping means 38 is also provided for limiting the motion of the second arm member 20, and thereby limiting flexion of the limb. The flexion stopping means is positioned between the first arm member 18 and the second arm member 20, and includes a second limit stop 40 having at least one pierced hole 42 and one tapped hole 44. Each pierced hole 42 is alignable with the interior rounded recessed track 16 of the base 12, and the tapped hole 44 simultaneously alignable with the associated indentation 14. Pins 30, equal to the number of pierced holes 42, are inserted into the pierced holes 42, and extend into the interior rounded recessed track 16 of the base 12. A flexion thumbscrew 48, or other manually insertable positive locking mechanism, is inserted into the tapped hole 44 and engages the associated indentation 14 so that rotation of the second arm member 20 can be limited. In the preferred embodiment, two pierced holes 42, with associated pins 30, and the tapped hole 44, with associated extension thumbscrew 48, form a three-point flexion locking mechanism. The flexion thumbscrew 48, can have a color coded flexion decal 50, and can have a swaged end 52 so as to prevent its removal from the second limit stop 40.

Preferably, the means 54 for securing the first and second arm members 18, 20 and the adjustable flexion and extension stopping means 22, 38 to the base 12 includes a cap 56 having an interior rounded recessed track 58 which mates with the interior rounded recessed track 16 of the base 12 (shown in FIG. 4), which, when mated with the base 12 forms a tunnel in which the the pins 30 travel, enabling the first and second limit stops 24, 40 to travel. A center rivet 60 secures the hinged limb immobilizer 10 through the center of the cap 56, the second arm member 20, and the base 12. Two rivets 62 pass through and connect the cap 56, the first arm member 18, and the base 12. A flexion/extension scaling decal 64 can be placed on the cap 56, for assisting in setting the degree of flexion/extension. Alternatively, the scale 64 can be placed directly on the cap 56 by stamping or some other permanent imprinting method.

The preferred means 66 for attaching the hinged limb immobilizer 10 to the limb is illustrated in FIG. 1, and includes pads 68 which circumscribe the upper and lower portions of the limb adjacent to the limb joint. Straps 70, preferably VELCRO, are inserted through apertures 72 in each arm member 18 and 20, and bind the hinged limb immobilizer 10 to the pads 68 and, hence, the limb.

Adjustment of the range of motion is accomplished by fully loosening the appropriate thumbscrew 32, 48, moving the appropriate limit stop 24, 40 to the desired location, and retightening the appropriate thumbscrew 32, 48 so that it extends through the appropriate indentation 14. Assuming at least a portion of the appropriate thumbscrew 32, 48 engages the indentation 14, positive locking is maintained even if the thumbscrew 32, 48 is not securely tightened.

SUMMARY OF THE ACHIEVEMENTS OF THE OBJECTS OF THE INVENTION

From the foregoing, it is readily apparent that we have invented a hinged limb immobilizer which provides a simple, logical method of setting and securely maintaining a predefined range of motion for a hinged limb immobilizer, requiring no special tools, provides security of adjustment using limit stops which embody both friction stop and positive stop characteristics, resulting in a unique "three-point locking" mechanism, provides separate color-coded, labelled scales for flexion and extension match-up with separate color-coded thumbscrews to avoid misunderstandings, and provides for simple manufacture by designing parts to be made from metal "stampings" instead of machined parts, thus resulting in consistent products at a controllable manufacturing cost.

It is to be understood that the foregoing description and specific embodiments are merely illustrative of the best mode of the invention and the principles thereof, and that various modifications and additions may be made to the device by those skilled in the art, without departing from the spirit and scope of this invention, which is therefore understood to be limited only by the scope of the appended claims.

We claim:

1. A hinged immobilizer for a limb, having adjustable extension stopping means and adjustable flexion stopping means, comprising:

(a) a base provided with circumferential indentations for receiving a manually insertable positive locking mechanism and an interior generally round recessed track for receiving pins carried by said extension stopping means and said flexion stopping means;

(b) a first arm member affixed to said base and extending outwardly from and parallel to said base;

(c) a second arm member pivotally connected to said base so that said second arm member is rotatable about the center of and parallel to said base;

(d) said adjustable extension stopping means carrying at least one pin engagable with said base for stopping said second arm member, said adjustable extension stopping means positioned between said first arm member and said second arm member, and comprises (i) a first limit stop having at least one pierced hole and one taped hole, each pierced hole being alignable with said interior rounded recessed track of said base, and said tapped hole is simultaneously alignable with said associated indentation;

(ii) pins, equal to the number of pierced holes, inserted into said pierced holes and which extend into said interior rounded recessed track of said base; and (iii) a manually insertable positive locking mechanism for insertion into said tapped hole and engagement with said associated indentation so that rotation of said second arm member cam be limited;

(d) said adjustable flexion stopping means carrying at least one pin engagable with said base for stopping said second arm member, said adjustable flexion stopping means positioned between said first arm member and said second arm member, and comprises (i) a first limit stop having at least one pierced hole and one tapped hole, each pierced hole being alignable with said interior rounded recessed track of said base, and said tapped hole is simultaneously alignable with said associated indentation;

(ii) pins, equal to the number of pierced holes, inserted into said pierced holes and which extend into said interior rounded recessed track of said base; and (iii) a manually insertable positive locking mechanism for insertion into said tapped hole and engagement with said associated indentation so that rotation of said second arm member can be limited;

(f) means for securing said first and second arm members and said adjustable extension and flexion stopping means to said base; and (g) means connectable to said arm member for attaching said hinged limb immobilizer to said limb.

2. The hinged limb immobilizer as set forth in claim 1, wherein said manually insertable positive locking mechanism is a thumbscrew.

3. The hinged limb immobilizer as set forth in claim 1, wherein the number of said pierced holes and the number of said pins equal two.

4. The hinged limb immobilizer as set forth in claim 1, wherein said manually insertable positive locking mechanism is provided with a color coded extension decal.

5. The hinged limb immobilizer as set forth in claim 1, wherein said manually insertable positive locking mechanism is swaged so as to prevent removal from said first limit stop.

6. The hinged limb immobilizer as set forth in claim 1, wherein the number of said pierced holes and the number of said pins equal two.

7. The hinged limb immobilizer as set forth in claim 1, wherein said manually insertable positive locking mechanism is provided with a color coded flexion decal.

8. The hinged limb immobilizer as set forth in claim 1, wherein said manually insertable positive locking mechanism is swaged so as to prevent removal from said first limit stop.

9. A hinged immobilizer for a limb, comprising:
(a) a base;
(b) a first arm member affixed to said base and extending outwardly from and parallel to said base;
(c) a second arm member pivotally connected to said base so that said second arm member is rotatable about the center of and parallel to said base;
(d) adjustable extension stopping means carrying at least one pin engagable with said base for stopping said second arm member;
(e) adjustable flexion stopping means carrying at least one pin engagable with said base for stopping said second arm member;
(f) means for securing said first and second arm members and said adjustable extension and flexion stopping means to said base, which comprises:
  (i) a cap having an interior rounded recessed track which mates with an interior rounded recessed track of said base, which, when mated with said base forms a tunnel in which said pins travel, enabling said first and second limit stops to travel;
  (ii) a center rivet securing said hinged limb immobilizer through the center of said cap, said second arm member, and said base; and
  (iii) two rivets passing through and fixedly connecting said cap, said first arm member, and said base; and
(g) means connectable to said arm members for attaching said hinged limb immobilizer to said limb.

10. The hinged limb immobilizer as set forth in claim 9, wherein said cap includes a flexion/extension scale for indicating the degree of flexion/extension.

11. The hinged limb immobilizer as set forth in claim 10, wherein said flexion/extension scale is a decal affixed to said cap.

12. The hinged limb immobilizer as set forth in claim 10, wherein said flexion/extension scale is integral with said cap.

13. A hinged immobilizer for a limb, comprising:
(a) a base;
(b) a first arm member affixed to said base and extending outwardly from and parallel to said base;
(c) a second arm member pivotally connected to said base so that said second arm member is rotatable about the center of and parallel to said base;
(d) adjustable extension stopping means carrying at least one pin engagable with said base for stopping said second arm member;
(e) adjustable flexion stopping means carrying at least one pin engagable with said base for stopping said second arm member;
(f) means for securing said first and second arm members and said adjustable extension and flexion stopping means to said base; and
(g) means connectable to said arm members for attaching said hinged limb immobilizer to said limb, which comprises:
  (i) pads which circumscribe upper and lower portions of said limb adjacent to a limb joint; and
  (ii) self-attaching straps for insertion through apertures in each arm member, which bind said hinged limb immobilizer to said pads and said limb.

* * * * *

UNITED STATES PATENT AND TRADEMARK OFFICE
CERTIFICATE OF CORRECTION

PATENT NO. : 5,000,169
DATED : March 19, 1991
INVENTOR(S) : George D. Swicegood, Henry L. Richbourg, Jr.

It is certified that error appears in the above—identified patent and that said Letters Patent is hereby corrected as shown below:

In claim 1, column 6, line 19, change "taped" to -- tapped --

In claim 1, column 6, line 31, change "cam" to -- can --

In claim 1, column 6, line 33, change "(d)" to -- (e) --

In claim 1, column 6, line 57, change "member" to -- members --

Signed and Sealed this

Tenth Day of May, 1994

*Attest:*

BRUCE LEHMAN

*Attesting Officer*     *Commissioner of Patents and Trademarks*